United States Patent [19]

Waitz et al.

[11] 4,367,287

[45] Jan. 4, 1983

[54] PROCESS OF PRODUCING ANTIBIOTIC AR-5 COMPLEX

[75] Inventors: J. Allan Waitz, Far Hills; Walter Reiblein, Verona; Imbi Truumees, Crestkill, all of N.J.

[73] Assignee: Schering Corporation, Kenilworth, N.J.

[21] Appl. No.: 310,191

[22] Filed: Oct. 9, 1981

Related U.S. Application Data

[63] Continuation of Ser. No. 93,080, Nov. 9, 1979, Pat. No. 4,307,085.

[51] Int. Cl.$^3$ .......................... C12P 19/62; C12R 1/29
[52] U.S. Cl. ........................................ 435/76; 435/867
[58] Field of Search .................................. 435/76, 867

[56] References Cited

U.S. PATENT DOCUMENTS 3,923,784  12/1975  Kierstead et al. ...................... 536/9
4,056,616  11/1977  Reimann et al. ...................... 536/17
4,171,314  10/1979  Chabala et al. ...................... 536/17
4,196,280  4/1980   Umezawa et al. ...................... 536/17

FOREIGN PATENT DOCUMENTS 2020647  11/1979  United Kingdom ................ 424/115

OTHER PUBLICATIONS

Satio et al., The Journ. of Antibiotics, vol. XXX111, No. 4, 1980 pp. 364-376.

Primary Examiner—Lionel M. Shapiro
Attorney, Agent, or Firm—Bruce M. Eisen; Gerald S. Rosen; Gerald F. Swiss

[57] ABSTRACT

The Antiboitic AR-5 complex is elaborated by a novel species of the Micromonospora; namely, *Micromonospora polytrota*. The microorganism also elaborates a number of minor components including the gentamicin complex and a complex of anthroquinone antibiotics.

2 Claims, No Drawings

… (1)

PROCESS OF PRODUCING ANTIBIOTIC AR-5 COMPLEX

This application is a continuation of application Ser. No. 093,080, filed Nov. 9, 1979, now U.S. Pat. No. 4,307,085, issued Dec. 21, 1981.

This invention relates to a novel composition of matter and to processes for the preparation, isolation, purification and the use thereof. More particularly, this invention relates to a novel antibiotic complex designated Antibiotic AR-5 and to its members, Antibiotic AR-5, component 1, Antibiotic AR-5, component 2, the 12,13-desepoxy derivatives of said components, to the nontoxic pharmaceutically acceptable acid addition salts, to the nontoxic pharmaceutically acceptable esters of said antibiotics and said derivatives and to the chemical conversion products of said antibiotic complex and said derivatives.

THE MICROORGANISM

The microorganism used according to this invention, *Micromonospora polytrota* is a novel species of the genus Micromonospora as can be determined by the description set forth below.

The microorganism was isolated from a soil sample collected in Campeche, Mexico. A culture of this microorganism has been made a part of the permanent collection of the Northern Utilization and Research Division, Agricultural Research Service, U.S. Dept. of Agriculture where it has been assigned accession number NRRL 12066. Subcultures of *Micromonospora polytrota* NRRL 12066 are available to the public from the aforementioned agency. A culture of this microorganism has been made a part of the collection of the American Type Culture Collection (ATCC) where it has been assigned accession number ATCC 31584. Subcultures of Micromonospora polytrota ATCC 31584 are available to the public from the ATCC.

*Micromonospora polytrota* (sometimes referred to as *M. polytrota*) is aerobic and grows well on a variety of solid and liquid nutrient media. It exhibits especially good growth and antibiotic production under submerged aerobic conditions.

The microorganism may be distinguished from other heretofore known species of the genus Micromonospora by a variety of taxonomical parameters. For example, *Micromonospora polytrota* forms spores, grows on D and L arabinose and fructose; fails to grow on rhamnose and D-xylose; utilizes citrate, formate, lactate and oxalate; grows in the presence of 50 mcg per milliliter of gentamicin, sisomicin, kanamycin, lincomycin and clindamycin; exhibits sensitivity to rosaramicin and chloramphenicol; hydrolyzes hypoxanthine and hippurate; does not hydrolyze xylan and chitin.

The microorganism also forms urease and allantionase; survives a temperature of 50° C. for eight hours; and exhibits resistance to phage 21.

Other distinguishing characteristics which aid in determining that *Micromonospora polytrota* is novel are its growth characteristics on various descriptive media.

The foregoing distinguishing characteristics were determined using the following procedures whose results are set forth in detail in the disclosure that follows.

Strain Maintenance

The initial source material was a freeze-dried preparation. The contents of the vial were suspended in 10 ml of broth consisting of yeast extract, 5 g; dextrose, 10 g; soluble starch, 20 g; NZ-Amine type A (Difco), 5 g; $CaCO_3$, 1 g; tap water, 1000 ml in 25 mm tubes stoppered with Morton closures. The pH was adjusted to 7.2 before autoclaving. The broth suspension was incubated at 30° C. on a rotary shaker (New Brunswick, Model G-52) at 250 rpm for 3 to 4 days. After growth, 5 ml of the resulting biomass was transferred into 50 ml of fresh medium having the composition described above in a 250 ml Erlenmeyer flask stoppered with cotton. Cultures were incubated as described above and harvested after 3 to 4 days. Five ml aliquots of the resulting biomass were asceptically dispensed into 17×60 mm sterile screw-capped vials and stored at −18° C.

Preparation of Inocula

One ml of thawed cell suspension was used to inoculate 25 mm tubes containing 10 m of the strain maintenance broth, incubated as described above, and a 5% inoculum transferred to two tubes of fresh broth. After three days at 30° C., the cells were harvested by centrifugation (Sorvall, Model GLC-1) at 450×g for 15 minutes in 15 ml graduated tubes, washed twice with sterile distilled water, and resuspended in water to three times the packed cell volume. The resulting washed suspension was used as inoculum for the taxonomy tests reported below.

A 1% transfer of *Micromonospora polytrota* was made into duplicate 25×150 mm tubes containing 10 ml of either a medium consisting of yeast extract, 1 g; soluble starch, 1 g; dextrose, 1 g; $CaCO_3$, 1 g; tap water, 1000 ml; a medium consisting of yeast extract, 10 g; soluble starch, 20 g; $CaCO_3$, 1 g; tap water, 1000 ml; a medium consisting of yeast extract, 5 g; dextrose, 10 g; $CaCO_3$; 1 g; tap water, 1000 ml or a medium consisting of yeast extract, 1 g; dextrose, 10 g; $CaCO_3$, 1 g; tap water, 1000 ml. Tubes were stoppered with Morton closures and incubated at 35° C. on a rotary shaker (New Brunswick Scientific, Model G-52) at 250 rpm. At 3, 5, 7 and 14 days, aliquots from the tubes were thinly spread onto the surface of glass cover slips, air dried and inverted onto a glass slide into a drop of dilute crystal violet solution (1:10 with distilled water). Slides were examined under the phase microscope at magnifications up to 2000 X.

*Micromonospora polytrota* was inoculated onto the surface of media in petri dishes of an agar consisting of yeast extract, 10 g; dextrose, 10 g; agar, 15 g; tap water, 1000 ml; pH 7.0, water agar consisting of tap water, 1000 ml; agar, 15 g; pH 7.0 and half-strength starch agar consisting of yeast extract, 1.5 g; potato starch, 5.0 g; distilled water, 1000 ml; agar, 15 g; pH 7.0. Duplicate plates of each medium were inoculated, incubated at 30° C. for 5, 10, 15, and 20 days and examined at each time period directly under the microscope. Representative plates were flooded with sterile tap water, the surface growth gently scraped and samples examined microscopically for motile spores. When aerial mycelia were observed, glass cover slips (1 mm) were dropped onto the surface of the growth, inverted onto a clean glass slide and examined under the microscope at a magnification of 1000 X.

Chemical Analysis of Whole Cells

The presence and form of diaminopimelic acid (DAP) and the presence of carbohydrates in whole-cell hydrolysates were determined by the methods of Becker et al (Appl. Microbial 12:421–423, 1964) and Lechevalier (J. Lab. Clin. Med. 71:934–944, 1968).

Growth Characteristics

*Micromonospora polytrota* was cultivated on standard actinomycete media as described by Shirling and Gottlieb (Int. J. Syst. Bacteriol 16:313–340, 1966) and Waksman 1. (The Actinomycetes, Williams and Wilkins Co., Baltimore, Md. 1961, Vol. 2, pp. 328–334). Plated media were inoculated and incubated for 14 to 21 days at 35° C. The color designations assigned to the vegetative mycelium pigments consisted of a color name 2. (Descriptive Color Names Dictionary, Taylor, H. D.; Knoche, L.; Granville, W. C., Container Corp. of America, 1950) and a color-chip number 3. (Color Harmony Manual, Ed. 4, Chicago, Container Crop. of America, 1958).

Utilization of Carbohydrates

To 5 ml of the sterile, molten basal carbohydrate medium consisting of yeast extract, 5 g; $CaCO_3$, 1 g; agar, 15 g; tap water, 1000 ml in 16×150 mm screw cap tubes, 0.5 ml of a 10% sterile solution of each test carbohydrate was added, the contents thoroughly mixed, and the tubes slanted. The slants were inoculated with *Micromonospora polytrota* using a sterile pipette. Tubes were observed for growth after 21 days at 35° C.

Decomposition of Organic Compounds

The decomposition of adenine, tyrosine, hypoxanthine, xanthine, xylan, urea, and allantoin were measured according to the procedures described by Lechenalier in the publication referred to herein above.

Chitin hydrolysis was measured using a modification of the procedure of Veldkamp. (Veldkamp H.: A study of the aerobic decomposition of chitin by microorganisms. Neded Landbouw Wageningen 55:127–174, 1955.) Ten ml of solidified water agar dispensed into 16×50 mm petri dishes was overlaid with 2.5 ml of colloidal chitin agar prepared as described below. Plates were inoculated with a streak down the center, incubated for 7, 14 and 21 days at 35° C. and examined for dissolution of the chitin.

Preparation of Colloidal Chitin

Following the procedure of Williams and Cross (Williams S. T., Cross, T.: Actinomycetes, in Booth C (ed) Methods in Microbiology, New York Academic Press 1971, pp. 295–334), crude chitin was alternately washed for 24 hours at a time with 1 N NaOH and 1 N HCl. The washing procedure was repeated five times after which the chitin was washed with 95% ethanol 3 to 4 times until all foreign matter was removed. The chitin was then air dried.

Fifteen g of the resulting cleaned chitin was moistened with acetone and then dissolved in 100 ml of cold concentrated HCl. The mixture was stirred for 20 minutes n an ice bath, and then filtered through a thin glass-wool pad in a Buchner funnel into 2 liters of stirred ice-cold distilled water. The chitin precipitated as a fine colloidal suspension. The residue was redissolved in concentrated HCl and refiltered until no more chitin was precipitated. The precipitated chitin was washed in 5 liters of distilled water four times. The pH was brought to 7.0 with 0.1 N NaOH.

The dry weight of the suspended chitin was determined and the suspension suitably diluted to prepare colloidal chitin agar (colloidal chitin, 2 g; agar, 20 g; distilled water, 1000 ml).

Hydrolysis of hippurate was determined using a modified Baird-Parker medium (sodium hippurate, 10 g; dextrose, 2 g; tryptone, 2 g; beef extract, 1 g; yeast extract, 2 g; $Na_2HPO_4$, 5 g; distilled water, 1000 ml; pH 7.0). The medium was dispensed in 10 ml aliquots into 25 mm tubes stoppered with Morton closures. Tubes were inoculated with the test culture, incubated at 30° C. on a rotary shaker at 250 rpm. After 7 and 14 days, the culture was tested for benzoic acid by mixing 1 ml of the culture broth, free of clumps, with 1.5 ml of 50% sulfuric acid in a 16 mm test tube. The appearance of crystals in the acid mixture after 4 hours at room temperature indicated hydrolysis of the hippurate.

Temperature Relationships

The ability of the test organisms to grow at 28° C., 35° C., 40° C. and 45° C. and to survive at 50° C. was tested on agar slants consisting of yeast extract, 5 g; dextrose, 10 g; soluble starch, 20 g; NZ Amine A (Difco), 5 g; $CaCO_3$, 1 g; agar, 15 g; tap water, 1000 ml employing the techniques outlined by Gordon et al (Gordon R. E.; Barnett D. A.; Henderhan J. E.; PANGCH: *Nocardia coeliaca, Nocardia autotrophica,* and nocardin strain. Int. J. Syst. Bacteriol 24:54–63, 1974).

Antibiotic Susceptibility of Producing Strain

Test antibiotics were dissolved in the appropriate solvent at a concentration based on an activity of 1000 mcg/ml. Stock solutions were diluted in sterile distilled water to a final concentration of 500 mcg/ml and filter sterilized (0.45 mm filters, Millipore Corporation). To 10 ml of the sterile antibiotic solutions, 90 ml of melted agar consisting of yeast extract, 10 g; dextrose, 10 g; agar, 15 g; tap water, 1000 ml; pH 2.0 cooled to 45° C. was added, and 20 ml of the resulting mixture was aseptically pipetted into sterile petri dishes (100×150 mm). The final concentration of each antibiotic in the agar was 50 mcg/ml.

Utilization of Organic Acids

Utilization of organic acids was determined using the procedures given by Gordon et al in the publication referenced hereinabove.

Resistance to Phage $\phi 21$

Preparation of Phage

Screw cap 25 mm tubes containing 20 ml of broth having the following composition (beef extract, 3 g; tryptone 5 g; dextrose, 1 g; soluble starch, 24 g; yeast extract, 5 g; $CaCO_3$, 2 g; tap water, 1000 ml; pH 7.5 with NaOH before sterilization) were fitted with sterile cotton plugged Pasteur pipettes. Tubes were inoculated with 0.5 ml of a thawed, frozen whole broth stock suspension of *M. purpurea* NRRL 2953. Air was bubbled into the tubes through the Pasteur pipette while the tubes were incubated at 30° C. in a water bath. After 24 hours, the tubes were inoculated with 0.1 ml of phage $\phi 21$ lysate obtained from Dr. D. Perlman (Univ. Wisconsin, Madison, Wis.), and incubated for an addition 48 hours. The tubes were centrifuged at a low speed to sediment the cell debris. The supernate containing the phage was decanted into sterile tubes and stored at 4° C. until use.

Inoculum Preparation

A 0.5 ml aliquot of a stock suspension of SCC 1410 was inoculated into tubes of broth set forth immediately above into which small glass rods (1 per tube) had been placed. The tubes were incubated for 26 hours at 35° C. on a rotary shaker at 250 rpm.

Test for Lysis

Petri dishes, 100×15 mm, were filled with 25 ml of sterile basal agar consisting of soluble starch, 20 g; dextrose, 10 g; yeast extract, 5 g; NZ Amine A, 5 g; CaCO$_3$, 1 g; agar, 15 g; distilled water, 1000 ml. After solidifying the agar, plates were left to dry overnight.

To 13 mm tubes containing 3 ml of melted, held at 47° C. soft basal agar (above medium with 7.5 g agar/liter), three drops of the 26 hr. test culture was added. The contents of the tube was shaken, poured over the basal agar and allowed to solidify. The plates were then drop inoculated with 0.01 ml of undiluted phage preparation and 10-fold serial dilutions in buffer (1 Na$_2$HPO$_4$, 6 g; KH$_2$PO$_4$, 3 g; MgSO$_4$.7H$_2$O, 0.2 g; NaCl, 0.5 g; NH$_4$Cl, 0.1 g; distilled water, 1000 ml to 10$^{-9}$). Plates were incubated for 3 days at 35° C. and examined for the formation of plaques.

Tolerance to Salts

Test concentrations of salts were weighed directly into 250 ml Erlenmeyer flasks then suspended in 10 ml of distilled water and autoclaved. To the flask, 90 ml of sterile, molten agar (whose composition is set forth under Antibiotic Susceptibility tests set forth above), cooled to 47° C., was added, the contents mixed to dissolve the salts thoroughly, and the mixture poured into sterile petri dishes. Duplicate plates were inoculated and examined for growth after 7, 14 and 21 days at 35° C.

Morphologically, some broth preparations of *Micromonospora polytrota* exhibit a vegetative mycelium formed in large clumps which are difficult to break up. The hyphae are fine, 0.8 to 1.2 microns and is abundantly branched. The branched hyphae exhibit swelling which form unusual type structures. Spores are not formed to any substantial degree in the broth media utilized even after 10 days incubation. When present, the spores occur singly along the length of the hyphae, either attached directly to the mycelium or on sporophores.

By contrast, abundant sporulaton is observed on the first and third (starch) agar media utilized in the morphological tests. Electron microscopic observation of the spore silhouettes revealed the presence of protrubances or warts along the spore surface.

Hydrolyzed whole cells contain the meso isomer of diaminopimelic acid. Arabinose and xylose are the characteristic sugars.

Macroscopic observations of the growth, or lack thereof, of *M. polytrota* on a variety of descriptive media are set forth on Table 1 below.

Macroscopic observations of the utilization, or lack thereof, of carbohydrates and organic acids by M. polytrota are set forth in Table 2 below.

Table 3 sets forth the growth, or lack thereof, of *M. polytrota* in the presence of representative antibiotics. The table also sets forth the microorganism's resistance to phage 21.

The table further sets forth the microorganism's growth, or lack thereof, in the presence of inorganic salts at various concentrations.

Additionally, Table 3 sets forth the microorganism's ability, or lack thereof, to hydrolyze a variety of compounds which are carbon and nitrogen sources.

TABLE 1
GROWTH CHARACTERISTICS OF *M. POLYTROTA* ON VARIOUS DESCRIPTIVE MEDIA

| Medium | Growth Characteristics |
| --- | --- |
| Bennett's Agar | G: +++, good |
| | S: Raised, granular |
| | AM: Present; gray bloom |
| | DFP: Present; gray-black |
| | C: gn, charcoal |
| Czapek-Sucrose Agar | G: +++, good |
| | S: Raised, plicate |
| | AM: Present, gray bloom |
| | DFP: Present, dark gray |
| | C: gp, black |
| Glucose-Asparagine Agar | G: ++, moderate |
| | S: Raised, granular |
| | AM: Absent |
| | DFP: Present, faint brown |
| | C: g5po, chocolate brown |
| Glycerol-Asparagine Agar (ISP No. 5) | G: +, fair to poor |
| | S: Granular |
| | AM: Absent |
| | DFP: Absent |
| | C: g41g, light spice brown |
| Nutrient Agar | G: +, fair to poor |
| | S: Granular |
| | AM: Absent |
| | DFP: Absent |
| | C: g41g, light spice brown |
| Potato Dextrose Agar | G: ++, moderate |
| | S: Raised, plicate |
| | AM: Present; white to gray bloom |
| | DFP: Absent |
| | C: g5ml, chocolate |
| Emerson's Agar | G: +, fair to poor |
| | S: Flat, granular |
| | AM: Absent |
| | DFP: Present, gray-brown |
| | C: g4pn, chocolate brown |
| NZA Glucose Agar | G: +++, good |
| | S: Raised, plicate |
| | AM: Present, white to gray bloom |
| | DFP: Present; absent |
| | C: gn, charcoal |
| Yeast Extract Glucose Agar | G: +++, good |
| | S: Raised, plicate |
| | AM: Present, white to gray |
| | DFP: Present, gray |
| | C: g8pn, ebony brown |
| Tomato Paste Oatmeal Agar | G: +++, good |
| | S: Raised, powdery |
| | AM: Present; gray bloom |
| | DFP: Present; faint-gray |
| | C: gd, gray |
| Yeast Extract - Malt Extract Agar (ISP No. 2) | G: +++, good |
| | S: Raised, plicate |
| | AM: Absent |
| | DFP: Present; gray |
| | C: g9pn, dark eggplant |
| Oatmeal Agar | G: +, fair to poor |
| | S: Granular |
| | AM: Present; white to gray bloom |
| | DFP: Absent |
| | C: g5po, chocolate |
| Water Agar | G: , poor |
| | S: Granular |
| | AM: Absent |
| | DFP: Absent |

TABLE 1-continued
GROWTH CHARACTERISTICS OF M. POLYTROTA ON VARIOUS DESCRIPTIVE MEDIA

| Medium | Growth Characteristics |
|---|---|
| | C: g4pl, dark spice brown |
| Inorganic Salts - Starch Agar (ISP No. 4) | G: ++, moderate |
| | S: Flat, granular |
| | AM: Present; gray bloom |
| | DFP: Present; gray |
| | C: g5po, chocolate brown |
| Starch Agar (Waksman No. 21) | G: +, fair to poor |
| | S: Flat |
| | AM: Present; white to gray bloom |
| | DFP: Present; gray |
| | C: g4nl, dark brown |
| Calcium Maleate Agar | G: +, fair to poor |
| | S: Granular, raised |
| | AM: Absent |
| | DFP: Absent |
| | C: g4pg, dark luggage tan |
| Tyrosine Agar (ISP NO. 7) | G: ++, moderate |
| | S: Raised, plicate |
| | AM: Absent |
| | DFP: Present; gray brown |
| | C: g8pn, ebony brown |
| Starch Agar (Gordon) | G: +++, good |
| | S: Raised, plicate |
| | AM: Present; gray bloom |
| | DFP: Present; faint brown |
| | C: g10po, black plum |
| Casein Agar (Gordon) | G: ++, moderate |
| | S: Flat, granular |
| | AM: Present; gray |
| | DFP: Present; yellow |
| | C: g5pi, copper brown |
| Gelatin Agar (McDade) | G: +, fair to poor |
| | S: Granular |
| | AM: Absent |
| | DFP: Absent |
| | C: g4nl, dark brown |

G = Growth; S = Surface characteristics; AM = Aerial mycelium; DFP = Diffusable pigments; and C = Color of the growth

TABLE 2
PHYSIOLOGIC PROPERTIES OF M. POLYTROTA

| Test | M. polytrota |
|---|---|
| Utilization of Carbohydrates: | |
| D-Arabinose | +++, good |
| L-Arabinose | +++, good |
| Cellibiose | +++, good |
| Dulcitol | −, poor |
| Erythritol | −, poor |
| Fructose | +++, good |
| L-Fucose | −, poor |
| Galactose | , poor to fair |
| Glucose | +++, good |
| -m-d-glucoside | −, poor |
| Glucerol | −, poor |
| Inositol | −, poor |
| Inulin | −, poor |
| Lactose | −, poor |
| Maltose | +++, good |
| Mannitol | −, poor |
| Mannose | +++, good |
| Melibiose | −, poor |
| Raffinose | −, poor |
| Rhamnose | −, poor |
| Ribose | +, fair |
| Sucrose | +++, good |
| Trehalose | +++, good |
| D-zylose | −, poor |
| Utilization of Organic Acids: | |
| Acetate | + |
| Benzoate | − |
| Butyrate | + |
| Citrate | + |
| Formate | + |
| Gluconate | − |
| Glucuronate | + |
| Glutamate | + |
| Lactate | + |
| Oxalate | + |
| Propionate | + |
| Pyruvate | + |
| Succinate | − |

TABLE 3

| Test | M. polytrota |
|---|---|
| Growth in the Presence of: 50 mcg/ml | |
| Gentamicin | + |
| Sisomicin | + |
| Neomycin | − |
| Kanamycin | + |
| Streptomycin | − |
| Erythromycin | − |
| Halomicin | − |
| Everninomicin | − |
| Rosaramicin | − |
| Cycloserine | − |
| Tetracycline | − |
| Penicillin G | − |
| Lincomycin | +++ |
| Clindamycin | +++ |
| Cephalothin | − |
| 10 mcg/ml | |
| Rosaramicin | − |
| Chloramphenicol | − |
| Streptomycin | − |
| Resistance to Phage 021: | |
| Growth in the Presence of: | |
| NaCl 1.0 | +++, good |
| 2.0 | +, fair to poor |
| 3.0 | −, no growth |
| $Na_2S_2O_3$ 1% | ++, moderate |
| 2% | −, no growth |
| 3% | −, no growth |
| 4% | −, no growth |
| Hydrolysis of: | |
| Adenine | − |
| Hypoxanthine | +, strong |
| Tyrosine | − to , very weak |
| Xanthine | − |
| Xylan | − |
| Chitin | − |
| Casein | + |
| Starch | + |
| DNA | + |
| Gelatin | + |
| Hippurate | + |
| Cellulose | − |
| Breakdown of: | |
| Urea 7d | + |
| 28 d | + |
| Allantoin | + |
| Nitrate Nitrite: | + |
| Growth at: | |
| 27° C. | ++, moderate |
| 35° C. | +++, good |
| 40° C. | ±, poor |
| 45° C. | −, no growth |
| 50° C./8 hours | ++, good |
| Litmus Milk: | No reaction |

TABLE 4

DESCRIPTION OF COLONIES OF *M. ECHINOSPORA* NRRL 2985, *M. PURPUREA* NRRL 2953, AND *M. ROSARIA* NRRL 3718 COMPARED TO *M. POLYTROTA*

| Medium | *M. polytrota* | *M. echinospora* * NRRL 2985 | *M. purpurea* * NRRL 2953 | *M. rosaria* + NRRL 3718 |
|---|---|---|---|---|
| Bennet's Agar | Growth good, color: charcoal, gn. | Growth good, color: deep maroon, g 7 ½ pl. | Growth good, color: terra cotta, m5pe. | Growth good, color: dark brown, g5pn. |
| Emerson's Agar | Growth fair, color: chocolate brown, g4pn. | Growth good, color: tile red, g5ne. | Growth good, color: burnt orange, g5nc. | Growth fair, color: dark brown, mahogany, m6pn. |
| Tomato Paste-Oatmeal Agar | Growth good, color: gray, gd. | Growth fair, color: dusty orange, g4lc. | Growth good, color: burnt orange, g5ne. | growth fair, color: dark brown, g4pn. |
| Glucose-Asparagine Agar | Growth moderate, color: chocolate brown, g5po | Growth, poor. | Growth fair, color: bright peach, g5la. | Growth poor. |
| Yeast Extract-Glucose Agar | Growth good, color: ebony brown, g8pn. | Growth, good, color: maple, g4le. | Growth good, color: deep brown, g4pl. | Growth good, color: copper brown, g5pi. |
| NZA-Glucose Agar | Growth good, color: charcoal, gn. | Growth good, color: burgundy, g 7½ pl. | Growth good, color: burgundy, g 7½ pl. | Growth moderate, color: rust tan, g5le. |

TABLE 5

DISTINGUISHING PHYSIOLOGIC PROPERTIES OF *MICROMONOSPORA POLYTROTA M. ECHINOSPORA, M. PURPUREA,* AND *M. ROSARIA*

| Test | *M. sp. polytrota* | *M. echinospora* | *M. purpurea* | *M. rosaria* |
|---|---|---|---|---|
| Carbohydrate Utilization: | | | | |
| D-Arabinose | +++, good | ±, poor | ±, poor | +++, good |
| L-Arabinose | +++, good | +++, good | +++, good | +++, good |
| Fructose | +++, good | ±, poor | ±, poor | ++, moderate |
| Galactose | ±, poor | ±, poor | ±, poor | +, fair |
| α-m-d-glucoside | −, poor | −, poor | −, poor | +, fair |
| Mannitol | −, poor | −, poor | −, poor | +++, good |
| Rhamnose | −, poor | +++, good | −, poor | +++, good |
| Ribose | +, fair | ±, poor | +, fair | +++, good |
| D-Xylose | −, poor | +++, good | +++, good | +++, good |
| Organic Acid Utilization: | | | | |
| Citrate | + | − | − | − |
| Formate | + | ± | ± | − |
| Gluconate | − | + | + | + |
| Lactate | + | + | + | − |
| Oxalate | + | − | − | − |
| Growth in the Presence of: | | | | |
| 50 mcg/ml | | | | |
| Kanamycin | + | + | + | − |
| Erythromycin | − | − | − | + |
| Everninomicin | − | − | − | + |
| Rosaramicin | − | − | − | + |
| Lincomycin | + | − | − | + |
| Clindamycin | + | − | − | + |
| Growth in the Presence of: | | | | |
| 10 mcg/ml | | | | |
| Rosaramicin | − | + | + | + |
| Chloramphenicol | − | + | + | − |
| Hydrolysis of: | | | | |
| Hypoxanthine | + | − | − | − |
| Tyrosine | ±very weak | + | + | + |
| Xylane | − | + | + | + |
| Chitin | − | + | + | + |
| Hippurate | + | − | − | − |
| Urease 7 d | + | − | − | + |
| 28 d | + | − | − | + |
| Allantoinase | + | − | − | − |
| Temperature: | | | | |
| 40° C. | ±, poor | ++, moderate | ++, moderate | ++, moderate |
| 50° C./8 hours | +++, good | ±, poor | ±, poor | +, fair |
| Resistance to Phage φ21: | +++ | +++ | − | N.D. |
| Sporulation Pattern: | | | | |
| Broth | Poor, 7–10 days | Poor, 7–10 days | Poor, no spores formed | Good, 5–7 days |
| Agar | Good, 7 days | Good, 7 days | Poor, no spores | Good, 7 days |

TABLE 5-continued

**DISTINGUISHING PHYSIOLOGIC PROPERTIES OF *MICROMONOSPORA POLYTROTA M. ECHINOSPORA, M. PURPUREA, AND M. ROSARIA***

| Test | M. sp. polytrota | M. echinospora | M. purpurea | M. rosaria |
|---|---|---|---|---|
| Spore Morphology: | Slightly warty | Warts spike like 0.1 micron in length | formed No spores | Slightly warty |

TABLE 6

**DISTINGUISHING PHYSIOLOGIC PROPERTIES OF *MICROMONOSPORA SP. POLYTROTA M. ECHINOSPORA, M. PURPUREA, AND M. ROSARIA***

| Test | M. sp. polytrota | M. echinospora | M. purpurea | M. rosaria |
|---|---|---|---|---|
| Carbohydrate Utilization: | | | | |
| D-Arabinose | +++, good | , poor | , poor | +++, good |
| L-Arabinose | +++, good | +++, good | +++, good | +++, good |
| Fructose | +++, good | , poor | , poor | ++, moderate |
| Galactose | , poor | , poor | , poor | +, fair |
| -m-d-glucoside | −, poor | −, poor | −, poor | +, fair |
| Mannitol | −, poor | −, poor | −, poor | +++, good |
| Rhamnose | −, poor | +++, good | −, poor | +++, good |
| Ribose | +, fair | , poor | +, fair | +++, good |
| D-Xylose | −, poor | +++, good | +++, good | +++, good |
| Organic Acid Utilization: | | | | |
| Citrate | + | − | − | − |
| Formate | + | | | − |
| Gluconate | − | + | + | + |
| Lactate | + | + | + | − |
| Oxalate | + | − | − | − |
| Growth in the Presence of: | | | | |
| 50 mcg/ml | | | | |
| Kanamycin | + | + | + | + |
| Erythromycin | − | − | − | + |
| Everninomicin | − | − | − | + |
| Rosaramicin | − | − | − | |
| Lincomycin | + | − | − | |
| Clindamycin | + | − | − | |
| Growth in the Presence of: | | | | |
| 10 mcg/ml | | | | |
| Rosaramicin | − | + | + | |
| Chloramphenicol | − | + | + | |
| Hydrolysis of: | | | | |
| Hypoxanthine | + | − | − | |
| Tyrosine | very weak | + | + | |
| Xylane | − | + | + | |
| Chitin | − | + | + | |
| Hippurate | + | − | − | |
| Urease 7 d | + | − | − | |
| 28 d | + | − | − | |
| Allantoinase | + | − | − | |
| Temperature: | | | | |
| 40° C. | , poor | ++, moderate | ++, moderate | |
| 50° C./8 hours | +++, good | , poor | , poor | |
| Resistance to Phage 21: | +++ | +++ | − | |
| Sporulation Pattern: | | | | |
| Broth | Poor, 7-10 days | Poor, 7-10 days | Poor, no spores formed | |
| Agar | Good, 7 days | Good, 7 days | Poor, no spores formed | |
| Spore Morphology: | Slightly warty | Warts spike like 0.1 micron in length | No spores | |

THE FERMENTATION

The antibiotics of this invention are elaborated when the *M. polytrata* non-sp. is fermented under controlled, submerged, aerobic conditions in an aqueous nutrient medium containing assimilable sources of carbon and assimilable sources of carbon and assimilable sources of nitrogen. Exemplory of such assimilable carbon sources are the carbohydrates. Exemplory of such assimilable sources of nitrogen are extracts from proteins. Preferred carbohydrates are tryptose, starch, dextrose, cerelose, mannitol glucose and the like. Preferred nitrogen sources are corn steep liquor, yeast extract, soybean meal, meat peptones, casein hydrolysate and the like.

The pH of the fermentation and of the vegetative inoculum is adjusted prior to inoculation and is, preferably, maintained at from about 60 to about 8.5 by the incorporation of a buffer such as calcium carbonate in the fermentation medium or in the vegetative inoculum. The preferred pH range is from about 6.8 to about 7.2.

Production of the antibiotics of this invention may be effected at most temperatures conducive to satisfactory growth of the microorganism; e.g. between 20° C. and 40° C., preferably between 27° C. and 35° C. The most preferred temperature in which to prepare the vegetative inoculum and to conduct the fermentation is about 30° C.

In general, the nutrient media are prepared in a suitable fermentation vessel or flask, is sterilized and cooled prior to inoculation. However, the media may be stored under aseptic conditions at low temperatures prior to use.

INOCULUM PREPARATION

In order to produce the antibiotics of this invention, a vigorously growing vegetative inoculum is preferred. In general, inoculum preparation is carried out in two or more stages. For large scale fermentations (e.g. about 50 liters), it is preferred that the inoculum be prepared in three stages.

Suitable media for preparing vegetative inocula are as follows:

| Medium A | | Medium B | |
|---|---|---|---|
| Beef Extract | 3 g | Potato Dextrin PD650 | 50 g |
| Tryptose | 5 g | Soy Grits | 35 g |
| Dextrose | 1 g | Dextrose | 5 g |
| Potato Starch | 24 g | Calcium Carbonate | 7 g |
| Yeast Extract | 5 g | Cobalt Chloride | 238 g |
| Calcium Carbonate | 2 g | Tap Water to | 1.0 liter |
| Tap Water to | 1.0 liter | | |

Two ml of freshly thawed whole broth of *M. polytrota* is used to inoculate 50 ml of sterile medium A.

A. The flask is incubated at about 30° C. for from about 48 to about 96, preferably about 72 hours on a gyratory shaker at about 300 rpm and a 2 inch throw.

SECOND INOCULUM STAGE

Twenty-five ml of the first inoculum is used to inoculate a series of 500 ml portions of sterile Medium B in two liter Erlenmeyer flasks. The flasks are incubated with gyratory agitation at about 30° C. for from about 24 to about 72, preferably 48 hours.

THIRD INOCULUM STAGE

Twenty-five ml of the second inoculum is used to inoculate each of a series of 500 ml portions of sterile Medium B in two liter Erlenmeyer flasks. The flasks are incubated with gyratory agitation at about 30° C. for from about 24 to about 72, preferably 48 hours.

The following medium has been found to provide both satisfactory and reproducible yields of antibiotic production.

| Medium C | |
|---|---|
| Staley J Starch | 50 g |
| Distillers Solubles | 7.5 g |
| Pharamedia | 5.0 g |

| Medium C -continued | |
|---|---|
| Cerelose | 5.0 g |
| Tap water to | 1.0 liter |

ANTIBIOTIC PRODUCTION

Ten liters of sterile Medium C is inoculated with 500 ml of second stage inoculum prepared as described above. Incubate the fermentation mixture at from about 27° to about 35° C., preferably about 30° C. with rotary agitation and aeration at about 350 rpm and at 0.35 vvm, respectively. Maintain the pH of the fermentation at from about 6.8 to about 7.2 by the addition of dilute alkali.

The fermentation is permitted to proceed for from about 48 to about 84, preferably about 72 hours before commencing to monitor for antibiotic activity. To monitor the fermentation, a sample of the whole broth is withdrawn and broth extracted with a water immiscible organic solvent. Exemplary of such solvents are methylene chloride, chloroform, benzene, toluene, ethyl acetate, amyl acetate or the like. The preferred solvent is ethyl acetate. The monitoring is conducted by thin layer chromatography on a silica gel using the lower phase of a solvent system consisting of chloroform:methanol:petroleum ether:water in the ratio by volume of 3:3:1:1. Quantitation of antibiotic production may be made using High Pressure Liquid Chromatography (HPLC) or other analytical techniques known in the art.

ISOLATION AND SEPARATION

When peak antibiotic production is attained, the Antibiotic AR-5 Complex may be isolated by extraction as described in the monitoring procedure using about two volumes of immiscible organic solvent per extract and by extracting the broth twice. The extracts are combined, evaporated to a residue and dissolved in methanol. Precipitation of the product by the addition of petroleum ether to the methanol solution yields the Antibiotic AR-5 complex.

Separation of the antibiotic complex into its components is effected by chromatography on Sephadex LH-20 using a concentrate of an ethyl acetate extract. Elution of the bioactive material is effected with ethanol. The ethanol eluate containing the bioactive fractions is concentrated and absorbed onto a silica gel column. Elution is effected using the previously described chloroform, methanol, petroleum ether and water system. The column is monitored by the use of thin layer chromatography using silica gel plates and the solvent system being used to elute the column. Fractions having $R_f$ of 0.51 and 0.43 contain the antibiotics of this invention.

THE ANTIBIOTICS

As stated previously, the compounds of this invention consist of two distinct antibiotic complexes. Of the two, one complex was previously known, that complex being gentamicin and is also sometimes referred to as the gentamicin C complex. Gentamicin consists of three distinct entities, namely gentamicin $C_1$, gentamicin $C_{1a}$ and gentamicin $C_2$.

The second antibiotic complex, and the one to which this disclosure is primarily directed, is the Antibiotic AR-5 complex (sometimes referred to as AR-5). This complex consists of four entities which have been designated Antibiotic AR-5 component-1, Antibiotic AR-5 component-2, 12,13-desepoxy AR-5 component-1 and 12,13-desepoxy AR-5 component-2. The term "Antibiotic" is also sometimes omitted from the names of the compounds of this invention.

PHYSIOCOCHEMICAL PROPERTIES OF THE ANTIBIOTICS

Based upon classical chemical analyses such as nuclear magnetic resonance (NMR) spectrometry, infrared spectroscopy (IR), ultraviolet spectroscopy (UV), mass spectroscopy (MS) and also upon chromatography against known antibiotics, it was determined that the members of the AR-5 complex are macrolides. Hydrolysis of the individual components established the presence of two sugars, mycinose and desosamine. Both of the sugars have been found to be constituents of other well known antibiotics. However, they may not heretofore been found to be constituents of the same macrolide antibiotic and in the same positions.

TABLE 7

| I Empirial Formulae | Molecular Weights |
| --- | --- |
| AR-5 component-1 | $C_{37}H_{61}NO_{12}$ MW 711 |
| AR-5 component-2 | $C_{37}H_{61}NO_{13}$ MW 727 |
| 12,13-desepoxy AR-5 component-1 | $C_{37}H_{61}NO_{11}$ MW 695 |
| 12,13-desepoxy AR-5 component-2 | $C_{37}H_{61}NO_{12}$ MW 711 |

II Nuclear Magnetic Spectra[1]

| Proton | AR-5 component-1[2] | 12,13-desepoxy[3] AR-5 component-1 |
| --- | --- | --- |
| =CH(2) | 5.88d(15.0) | 5.93 |
| =CH(11) CH— = (Four) | 6.55 | CH=(six) 6.18 |
| =CH(3) | 6.68 | 6.60 |
|  |  | 6.98 |
| =CH(10) |  | 7.02 |
| =CH15 | 5.36m | 4.97m |
| OCHO Mycinose | 4.59d (8.0) | 4.58d (8.0) |
| OCHO desosamine | 4.38d (7.0) | 4.30d (7.5) |
| OCHO |  |  |
| OCH3 (two) | 3,58,363 singlets | 3.48, 3.54 singlets |
| CH |  |  |
| N(CH3)2 | 2.28s | 2.28s |
| CH2(16) |  |  |
| CH2(7) |  |  |
| CH3(4) |  | 1.22d(7.0) |
| CH3(three) |  | 1.14d,1.14d,1.18d |
| CH3 | 1.02d(6.5) | 1.00t(6.5) |
| CH3(C—16CH3) | 0.88t(7.0) | 0.92t(7.0) |

TABLE 8

| Proton | AR-5 component-2[4] |
| --- | --- |
| =CH(2) | 6.96d(15.0) |
| =CH(11) CH— (Four) | 6.66d(15.0, 10.0) |
| =CH(3) | 6.38dd(15.0, 9.0) |
| =CH(10) | 6.09d(15.0) |
| =CH15 | 5.44d(8.5, 5.5) |
| OCHO Mycinose | 4.62d(8.0) |
| OCHO desosamine | 4.32d(7.0) |
| OCHO | 3.84 |
|  | 3.76 |
| OCH3 (two) | 3.56S, 3,56S |
| CH | 3.18 |
|  | 2.50 |
| N(CH3)2 | 2.28 |
| CH2(16) | 1.80m |
| CH2(7) | 1.70m |
| CH3(4) | 1.26d(7.0) |
| CH3(three) | 1.18d(6.5) |

TABLE 8-continued

| Proton | AR-5 component-2[4] |
| --- | --- |
| CH3 | 1.04d(6.5) |
| CH3(C—16CH3) | 0.86t(7.0) |

[1]100 MHz Proton NMR
[2]Solvent (CD3)2CO
[3]Solvent CDCl3
[4]Solvent CDCl3

TABLE 9

| Ultraviolet | |
| --- | --- |
| Antibiotic AR-5 Component 1 | |
| max | |
| 271 nm $E^1$ % = 329 (= 23,400) | |
| 245 $E^1$ % = 170 (= 12,070) | |
| Antibiotic AR-5 Component 2 | |
| max | $[\alpha]^{26° C.} = 22.9$ ($C_2H_5OH$) |
| 216 nm $E^1$ % = 324 (= 23,390) | |
| 246 nm $E^1$ % = 138 (= 10,000) | |
| 12,13-desepoxy AR-5 Component 1 | |
| max | $[\alpha]^{26° C.} = 7.2$ ($C_2H_5OH$) |
| 214 nm $E^1$ % = 290 (= 20,160) | |
| 280 nm $E^1$ % = 295 (− 20,500) | |
| 12,13-desepoxy AR-5 Component 2 | |
| max | $[\alpha]^{26} = 68.1$ ($CHCl_3$; 0.3%) |
| 214 nm = (20,067) | |
| 278 nm − (19,702) | |

TABLE 10

COMPARATIVE THIN LAYER CHROMATOGRAPHY ANTIBIOTIC OF AR-5 COMPLEX WITH SOME MACROLIDE ANTIBIOTICS

| System | Antibiotic | $R_f$ of Inhibition Zone |
| --- | --- | --- |
| Chloroform-Methanol-17% Ammonia 2:1:1 | Antibiotic AR-5 Complex | 0.98 |
|  | Rosaramicin | 0.98 |
|  | Megalomicin | 0.97 |
|  | Oleandomycin | 0.95 |
|  | Erythromycin | 0.94 |
|  | Spiramycin | 0.95 |
|  | Magnamycin | 0.96 |
| Butanol-Acetic Acid-Water-Dioxane 6:2:2:1 | Antibiotic AR-5 Complex | 0.5 |
|  | Rosaramicin | 0.41 |
|  | Oleandomycin | 0.39 |
|  | Erythromycin | 0.45 |
|  | Spiramycin | 0.32 |
|  | Magnamycin | 0.59 |
| Chloroform-Methanol-Petroleum Ether-Water 3:3:1:1 | Antibiotic AR-5 component 1 | 0.51 |
|  | Antibiotic AR-5 component 2 | 0.43 |
|  | Rosaramicin | 0.40 |
|  | Oleandomycin | 0.34 |
|  | Erythromycin | 0.34 |
|  | Spiramycin | 0.53 |
|  |  | 0.58 |
|  | Magnamycin | 0.75 |
| Butanol-Acetic Acid-Water 3:1:1 | Antibiotic AR-5 Complex | 0.46 |
|  | Rosaramicin | 0.41 |
|  | Megalomicin | 0.38 |
|  | Oleandomycin | 0.41 |
|  | Erythromycin | 0.48 |
|  | Spiramycin | 0.23 |
|  | Magnamycin | 0.59 |

In the foregoing Chromatographic Comparisons it should be noted that none of the systems completely separates the antibiotics of this invention from each other. They do, however, serve to distinguish the Antibiotic AR-5 Complex from some of the known macrolides.

CHARACTERISTIC INFRARED ABSORPTION PEAKS

The characteristic infrared absorption peaks are set forth as wave number values and are accurate within 3 $cm^{-1}$. The spectra were obtained on a Perkin-Elmer Model 180 I.R. grating spectophotometer as solutions in chloroform.

The legends (letters) set forth have the following meanings: s=strong; m=medium; w=weak and vs=very strong.

TABLE 11

| Antibiotic AR-5 Component 1 | | Antibiotic AR-5 Component 2 | |
|---|---|---|---|
| 3540 $cm^{-1}$ | (m) | 3540 $cm^{-1}$ | (m) |
| 3420 | (m) | 3430 | (m) |
| 2975 | (m) | 2980 | (m) |
| 2940 | (m) | 2940 | (m) |
| 2885 | (m) | 2885 | (m) |
| 2790 | (m) | 2795 | (m) |
| 1710 | (m) | 1715 | (m) |
| 1690 | (m) | 1715 | (m) |
| 1650 | (m) | 1690 | (m) |
| 1675 | (m) | 1655 | (m) |
| 1595 | (m) | 1630 | (m) |
| 1235 | (m) | 1610 | (shoulder (m)) |
| 1220 | (shoulder (m)) | 1240 | (m) |
| 1165 | (s) | 1230 | (shoulder (m)) |
| 1110 | (s) | 1175 | (s) |
| 1095 | (shoulder (m)) | 1110 | (s) |
| 1072 | (vs) | 1085 | (vs) |
| 1050 | (shoulder (vs)) | 1060 | (vs) |
| 985 | (s) | 990 | (s) |
| 885 | (m) | 890 | (m) |
| 860 | (m) | 865 | (m) |
| 830 | (m) | 840 | (m) |

| 12,13-desepoxy AR-5 Component | | 12-13-desepoxy AR-5 Component 2 | |
|---|---|---|---|
| 3540 $cm^{-1}$ | (m) | 3550 | (m) |
| 3420 | (m) | 3420 | (m) |
| 2975 | (m) | 2980 | (m) |
| 2940 | (m) | 2940 | (m) |
| 2885 | (m) | 2880 | (m) |
| 2795 | (m) | 2835 | (m) |
| 1710 | (m) | 2790 | (m) |
| 1675 | (m) | 1710 | (m) |
| 1650 | (m) | 1680 | (m) |
| 1630 | (m) | 1650 | (m) |
| 1595 | (m) | 1635 | (m) (shoulder) |
| 1230 | (m) | 1595 | (m) |
| 1225 | (shoulder (m)) | 1235 | (m) |
| 1165 | (s) | 1225 | (m) (shoulder) |
| 1110 | (s) | 1170 | (s) |
| 1050 | (vs) | 1110 | (s) |
| 1050 | broad) | 1095 | (s) (shoulder) |
| 1000 | (m) | 1072 | (vs) |
| 985 | (s) | 1050 | (vs) (shoulder) |
| 885 | (w) | 1000 | (m) |
| 860 | (w) | 985 | (s) |
| 840 | (w) | 910 | (w) |
| | | 885 | (w) |
| | | 860 | (w) |
| | | 845 | (m) |
| | | 835 | (m) |

On the basis of the foregoing physiochemical data and the isolation of mycinose and desesamine from the hydrolysis of the respective antibiotic compounds, it is concluded that the antibiotics of this invention have the following planar structural formulae:

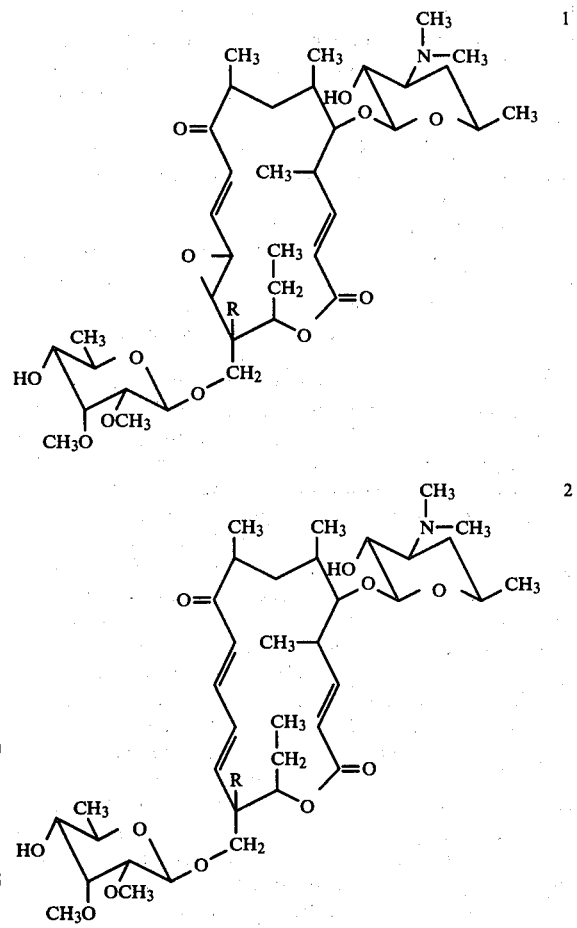

Wherein in formula 1, R is hydrogen in Antibiotic AR-5 component 1 and is hydroxyl in Antibiotic AR-5 component 2 and wherein in formula 2, R is hydrogen in 12,13-desepoxy AR-5 component 1 and is hydroxyl in 12,13-desepoxy Ar-5 component 2.

The hydroxyl groups at positions 2', 4" and in the case of antibiotics AR-5 Component -2 and 12,13-desepoxy AR-5 Component -2, the hydroxyl group attached to carbon 14 of the macrolide ring, are all amenable to esterification to form non-toxic pharmaceutically acceptable esters such as, for example, those formed by reaction with typical acylating agents such as anhydrides and chlorides of organic acids, especially hydrocarbon carboxylic acids. Further, the members of the antibiotic AR-5 complex are susceptible to the formation of 2'-monoesters, 2',4"-diesters and under certain conditions 14, 2',4"-triesters. The 4"-monoester is conveniently prepared by the solvolysis of a 2',4"-diester. In like manner, the 14-monoester is conveniently prepared by the hydrolysis of a 14, 2',4"-triester. The 2'-monoesters may be prepared directly by treating the free unesterified antibiotic with a stoichiometric quantity (or a slight excess) of an acylating agent, such as an acyl-halide or an acyl anhydride at about ambient temperature preferably in a non-reactive solvent such as acetone. The reaction is continued for from about 1 to about 20 hours until esterification is substantially complete and isolating the 2'-monoester from the reaction mixture.

In general, the 2',4"-diesters may be prepared directly by treating the free antibiotics with an excess of acylating agent at about ambient temperature for from about 1 to about 7 days until esterification is substantially complete and isolating the 2',4"-diester from the reaction mixture.

Alternatively, 2',4"-diesters may be prepared by treating a 2'-monoester with an excess of acylating agent under substantially the same conditions described above for direct esterification. This procedure is especially advantageous for preparing mixed esters wherein the desired compound has a different acyl function on each of positions 2' and 4". Such mixed esters are attractive since they offer a greater range variability in biological and formulation properties.

It is to be noted that the mono, di and tri-esters of this invention all have the further property of forming non-toxic pharmaceutically acceptable acid addition salts which have enhanced water solubility and are, therefore, useful for parenteral administration.

As used herein non-toxic pharmaceutically acceptable acid addition salts denote those generally employed in the pharmaceutical art. Embraced by the term are the salts formed with inorganic acids such as sulfuric, phosphoric and hydrohalic (e.g. hydrochloric) and those formed with carboxylic acids having 2 to 18 carbon atoms such as aliphatic, cycloaliphatic, aromatic and heterocyclic carboxylic acids including dicarboxylic acids. Exemplary of such acids are acetic, propionic, stearic, tartaric, maleic, cyclopropylcarboxylic, cyclopentylcarboxylic, adamantoic, furic, nicotinic, thenoic, picolinic, benzoic, phenylacetic and the like.

In like manner, the non-toxic pharmaceutically acceptable esters of this invention also embrace esters of the acids generally used in the pharmaceutical arts and includes esters of carboxylic acids having 2 to 18 carbon atoms. Embraced by the term are aliphatic, cycloaliphatic, aromatic and heterocyclic including the hemi esters formed with dicarboxylic acids such as maleic, malic, malonic acids and the like. Examples of such acids are set forth herein above as those suitable for preparing pharmaceutically acceptable acid addition salts.

In addition to the ester derivatives described above antibiotics AR-5-1 and AR-5-2 may be converted to their respective 12,13-desepoxy derivatives by treatment with chromous ions derived from a chromous salt of a mineral acid by substantially the procedure described in U.S. Pat. No. 3,975,372, issued Aug. 17, 1976. The disclosure of this patent is hereby incorporated by reference.

The antibiotics of this invention may be converted to a plurality of derivatives analogous to those described in U.S. Pat. No. 4,056,616, issued Nov. 1, 1977 whose disclosure is also incorporated by reference herein. For example, an antibiotic of this invention may be hydrogenated at the 9-position of the macrolide ring to form the corresponding 9, 9-dihydro derivative.

BIOLOGICAL ACTIVITY

The antibiotics of this invention were subjected to art recognized tests to determine their antibacterial profile. The test methodology and a summary of the results therefrom are set forth hereinbelow.

In order to place the antibacterial activity of the compounds of this invention in the proper perspective, Erythromicin and Rosaramicin were also subjected to the same tests.

In vitro broth dilution tests (MIC's) were done in conventional manner using either Mueller-Hinton broth (gram-positive and gram-negative bacteria), Sabouraud Dextrose Broth (fungi) or Fluid Thioglycollate broth (anaerobic bacteria) at the appropriate pH, in volumes of 3-5 ml/tube. Inocula were obtained by diluting either overnight cultures (gram-positive and gram-negative bacteria and yeasts), 48 hr. cultures (anaerobic bacteria), or 4-5 day cultures (dermatophytes). Tubes were incubated either at 28° C. (dermatophytes), 37° C. (gram-positive and gram-negative bacteria and yeasts), and endpoints were read after 24, 48 and 72 hours.

In vitro agar dilution tests were performed using Mueller-Hinton agar which was melted prior to use and cooled to approximately 55° C. before the addition of suitable volumes of compound solution, to provide two-fold serial dilutions. Thirty ml was transferred to $100 \times 15$ mm square "Integrid" petri dishes and allowed to dry overnight. Plates were inoculated with a Steers-Foltz replicating device. Inoculum concentrations were adjusted so that each inoculating rod of the Steers' replicator delivered approximately $10^4$ viable units of each organism to the agar surface. Inoculated plates were allowed to dry and then incubated at 37° C. MIC's were active determined after 24 and 48 hours of incubation. The MIC was the lowest concentration at which less than six isolated, discrete colonies were visible.

In the following Tables, the Antibiotics of this invention are set forth in the following order: Antibiotic AR-5 component 1 is A, 12,13-desepoxy AR-5 component 1 is B, Antibiotic AR-5 component 2 is C, 12,13-desepoxy AR-5 component 2 is D, Erythromycin is E and Rosaramicin is F:

| ANTIBACTERIAL MEAN MIC'S OF SELECTED MACROLIDES | | | | | | | |
|---|---|---|---|---|---|---|---|
| Organism | No. of Isolates | A | B | C | D | E | F |
| S. lutea | 1 | .06 | .06 | .06 | <.04 | .125 | .06 |
| B. subtilis | 2 | .09 | .17 | .18 | .25 | .35 | .71 |
| Staph. $E^SR^S$ | 13 | .075 | .080 | .123 | | .06 | .139 |
| $E^RR^S$ | 3 | .2 | 0.5 | 0.63 | | 256 | 2.5 |
| $E^RR^R$ | 5 | 111 | 111 | 194 | | 256 | 256 |
| Enterococcus | 4 | 14 | 19 | 32 | 4 | 0.5 | 0.8 |
| C. albicans | 2 | 256 | 256 | 256 | >32 | 256 | 256 |
| Enterobacter | 5 | 194 | 223 | 128 | >32 | 147 | 16 |
| E. coli | 13 | 55 | 75 | 25 | 16 | 22 | 5 |
| Klebsiella | 12 | 181 | 192 | 81 | >32 | 68 | 15 |
| Prov./Prot. (indole positive) | 12 | 192 | 203 | 144 | >32 | 228 | 31 |
| Pseudomonas | 20 | 187 | 187 | 187 | >32 | 158 | 74 |
| Salmonella | 5 | 223 | 256 | 147 | >32 | 97 | 11 |
| Shigella | 1 | 32 | 128 | 64 | 8 | 32 | 4 |
| Serratia | 9 | 220 | 256 | 188 | >32 | 138 | 19 |

The Staphylococcus isolates were divided into three groups: $E^SR^S$, erythromycin and rosaramicin sensitive strains, $E^RR^S$, erythromycin resistant and rosaramicin sensitive strains, $R^RR^R$, strains resistant to both erythromycin and rosaramicin. Only against the final group of macrolide resistant strains did the antibiotics of this invention lose activity. They were active against some strains anaerobes such as B. fragilis and Clostrida but did not show the gram-negative potency of rosaramicin.

In vivo mouse protection tests were performed in male (Carworth CF-1) mice weighing 18-20 g each. Infection was with about $10^7$ organisms per mouse or sufficient inocula to cause death of control groups 24 to 48 hours after infection. The infecting organisms included strains of *Staphylococcus Enterococcus*, β-hemolytic Streptococcus and *E. coli.*

The serum levels of the respective antibiotics were measured in mice, rats and dogs. The results were surprising in that the antibiotics of this invention exhibit therapeutic serum levels considerably longer than erythromycin or rosaramicin. It was also observed that Antibiotic AR-5 component 2 produces peak serum levels earlier than any of the other antibiotics tested, however, Antibiotic AR-5 component 1 produces therapeutic serum levels of greater duration. This phenomenon gives substantial support for pharmaceutical dosage forms containing both compounds. This would provide for fewer doses per day without sacrificing the therapeutic effect.

TABLE

| Route | Mean $PD_{50}$'s | | | | | |
|---|---|---|---|---|---|---|
| | A | B | C | D | E | F |
| Antibiotic AR-5 Sensitive (mg/kg) | | | | | | |
| s.c. | 4.0(7)* | 2.5(7) | 5.1(7) | — | 13.3(6) | 8.3(6) |
| oral | 4.1(7) | 3.8(7) | 35.8(7) | — | 135.0(6) | 181.0(6) |
| Antibiotic AR-5 Resistant | | | | | | |
| sc. | 100(5) | 100(5) | 100(5) | | 100(5) | 100(5) |
| oral | 100(5) | 100(5) | 100(5) | | 400(5) | 400(5) |

*Number of strains averaged is given in parentheses.

Comparative in vivo $PD_{50}$'s with erythromycin and rosaramicin demonstrated a major advantage that the compounds of this invention offer. Unlike erythromycin and rosaramicin, with one exception, the compounds of this invention appear to have equal potencies orally and subcutaneously. In general, Antibiotic AR-5 component 1 and 12,13-desepoxy component 1 were 30–40 fold more potent orally than erythromycin and rosaramicin.

The acute toxicity determinations were carried out with groups of male (Carworth CF-1) mice weighing 18-20 g. $LD_{50}$ values 1 the dose that was lethal to 50% of the mice) were calculated by probit analysis based on the number of survivors at 24 and 48 hours after dosing.

| Route | $LD_{50}$'s (mg/kg) | | | | | |
|---|---|---|---|---|---|---|
| | A | B | C | D | E | F |
| i.v. | 140 | 160 | 310 | — | 260 | 175 |
| i.p. | 310 | 275 | 610 | — | 355 | 260 |
| oral | 2000 | — | 2000 | — | — | 1300 |

By virtue of their in vivo activity, the antibiotics of this invention may be administered topically, parenterally and orally, preferably in admixture with suitable pharmaceutically excipients. These antibiotics may be administered in the form of the free underivatized compound or in the form of non-toxic pharmaceutically acceptable esters or in the form of non-toxic pharmaceutically acceptable acid addition salts.

The antibiotics of this invention need not be separated from each other in order to exhibit a substantial anti-bacterial effect, but may be used as the complex. A preferred combination is a pharmaceutical dosage form containing 30 to 60% preferably 40 to 50% of one of Antibiotic AR-5 Component 1 or Antibiotic AR-5 Component 2 in a dosage form in admixture with suitable pharmaceutical excipients and wherein the remainder of the antibacterially active material is the other of Antibiotic AR-5 Component 1 or Antibiotic AR-5 Component 2. An especially useful dosage form is a shaped solid one containing the aforementioned antibiotic components and suitable pharmaceutical excipients.

The dosage forms, excluding topicals, should be designed to permit the administration of from about 5 to about 50 mg per kg per day. Topical formulations should be applied to the affected areas from about 2 to about 4 times a day and should contain from about 5 to 15, preferably about 10 grams per liter for lotions and the same quantity per kilogram for ointments. However, it should be realized that many factors influence the precise dosage of a medicament to be administered. Such factors as the age and general physical condition of the patent, the nature of the infecting organism and the like must be considered. Thus, the ultimate decision regarding how much and how often must, within the limit of safety, be left to the practioner.

EXAMPLE 1

Preparation of The Antiboitic AR-5 Complex

Inoculum Preparation

Prepare 3.0 liters of second stage inoculum according to the procedure set forth above under the heading The Fermentation.

Fermentation

Six 14 liter fermenters containing 10 liters of Medium C are sterilized, cooled to 30° C. and inoculated with 500 ml of second stage inoculum. Incubate each fermentation mixture at 30° C. with rotary agitation at 350 rpm and aeration at 0.35 vvm. Adjust the fermentation mixture to pH 7 at the commencement of the fermentation and maintain at pH 7.0±0.5 by adding dilute alkali as required. Continue the fermentation for about 72 hours, them commence monitoring for antibiotic production.

Isolation and Purification of the Antibiotics

When peak production is attained, combine the six batches to form one 60 liter batch. Extract the combined batches two times with 120 liters of ethyl acetate. Concentrate the extracts to an oil in vacuo. Adsorb the oily residue on a column containing 2.1 liters as Sephadex LH-20 and elute with ethyl alcohol. Eluates containing antibacterially active fractions as determined by disc testing against *Staphylococcus aureus* 209P are combined, concentrated and absorbed onto a column containing 400 g of silica gel. Elute with the lower phase of a chloroform:methanol:petroleum either:water system (3:3:1:1). Monitor the eluate using HPTLC and combine fractions containing like materials.

Yield—913 mg Antibiotic AR-5 Component 1+12, 13-desepoxy-AR-5 Component 1

950 mg—Antibiotic AR-5 Component 2+12, 13 desepoxy-AR-5 Component 2.

Purification of the Antibiotics

Absorb 1.1 g of crude Antibiotic AR-5 Component 2 (contaminated with 12; 13-desepoxy AR-5 components 2) on a column containing 130 g of silica gel and elute as previously described to obtain thereby 297 mg of Antibiotic AR-5 component 2 HPLC Analysis greater than 95% pure. Combine and concentrate the remaining eluates to obtain thereby 12,13-desepoxy AR-5 component 2.

Repeat the above purification using 1.2 g of crude Antibiotic AR-5 Component 1 (contaminated with 12,13-desepoxy AR-5 Component 1) to obtain 400 mg of an oily, unresolved mixture. Subject 8.9 mg of this mixture to preparative HPLC using Partial M9 PAC as the stationary phase and using the lower phase of a methylene chloride:method:haptane:water (3:2:1) system to obtain 7.5 mg of 95% pure by HPLC. Combine the remaining eluates to obtain thereby 12,13-desexopy AR-5 component 1.

EXAMPLE 2

| Capsule | |
|---|---|
| Antibiotic AR-5 Component 1 | 250.00 mg |
| Lactose | 248.75 mg |
| Magnesium Stearate | 1.25 mg |
| | 500.00 mg |

Procedure
1. Blend the antibiotic and the lactose.
2. Add the magnesium stearate and mix.
3. Fill capsule.

EXAMPLE 3

| Oral Suspension (to give a dose of 125 mg/5 ml) | |
|---|---|
| Antibiotic AR-5 Component 2 | 25.00 gms |
| Magnesium Aluminum Silicate | 9.50 gms |
| Sodium Carboxymethylcellulose U.S.P. | 2.50 gms |
| Flavor | qs |
| Color | qs |
| Methylparaben, U.S.P. | 0.90 gms |
| Propylparaben, U.S.P. | 0.20 gms |
| Polysorbate 80, U.S.P. | 1.00 gms |
| Sorbitol Solution, U.S.P. | 500.00 gms |
| Water, q.s. | 1000.00 ml |

Procedure

1. Heat 200 ml. of water to boiling, and dissolve in it one half of the parabens. Cool to about 70° C., then mix in the Polysorbate 80. Sprinkle in the silicate, stirring until a uniform smooth suspension results.
2. Heat an additional 200 ml. of water to boiling, and dissolve in it the remainder of the parabens. Disperse the CMC in this until a smooth gel results. Mix in the Sorbitol Solution. Then dissolve the sodium citrate.
3. Add the product of Step 2 to that of Step 1 slowly, with constant stirring. Cool the mixture to 25° C. Add the Antibiotic AR-5 Component 2, tartrate flavor, and color mixing thoroughly. Add sufficient quantity of water to make the total volume 1000 ml.

EXAMPLE 4

| Topical Ointment | |
|---|---|
| 12,13-Desepoxy-AR-5 Component 1 | 10 gms |
| Petrolatum | 990 gms |
| | 1000 gms |

Procedure

1. Melt the petroleum.
2. Slurry the antibiotic with about 10% of the petrolatum and pass through a colloid mill.
3. Mix the milled slurry with the remainder of the molten petrolatum. Allow to cool.

EXAMPLE 5

| Topical Cream | |
|---|---|
| 12,13-Desepoxy-AR-5 Component 2 | 10 gms |
| Stearic Acid | 200 gms |
| Sorbitan Monostearate | 104 gms |
| Sorbitan Monoleate | 20 gms |
| Polyoxyethylene Sorbitan Monolaurate | 56 gms |
| Water, qs | 100 ml |

Procedure

1. Heat the stearic acid, sorbitan monostearate, sorbitan monoleate, and polyoxyethylene sorbitan monolaurate to 65° C.
2. Heat about 90% of the water to 70° C.
3. Add the water to Step 1 and mix to form a cream base.
4. Slurry the antibiotic with about 10% of the water and pass through a colloid mill.
5. Add the milled slurry to the molten base and mix. Allow to cool.

EXAMPLE 6

| Capsule | |
|---|---|
| Antibiotic AR-5 Component 1 | 125 mg |
| Antibiotic AR-5 Component 2 | 125 mg |
| Lactose | 248.75 mg |
| Magnesium Stearate | 1.25 mg |
| | 500.00 mg |

Procedure

1. Blend the antibiotics and the lactose.
2. Add the magnesium stearate and mix.
3. Fill capsule.

In the foregoing formulations, the antibiotics of this invention, the non-toxic, pharmaceutically acceptable esters and the non-toxic, pharmaceutically acceptable acid addition salts thereof may be used, in equivalent quantity, interchangeably without substantially modifying the therapeutic effect to be derived from their use.

We claim:

1. A process which comprises cultivating an antibiotic AR-5 producing strain of *Micromonospora polytrota* nov. sp. in an aqueous nutrient medium under controlled submerged aerobic conditions until a composition having substantial antibiotic activity is produced and removing an antibiotic selected from the group consisting of antibiotics AR-5 component 1; AR-5 component 2; 12,13-desepoxy AR-5 component 1; 12,13-desepoxy AR-5 component 2 having the following planar structural formulae:

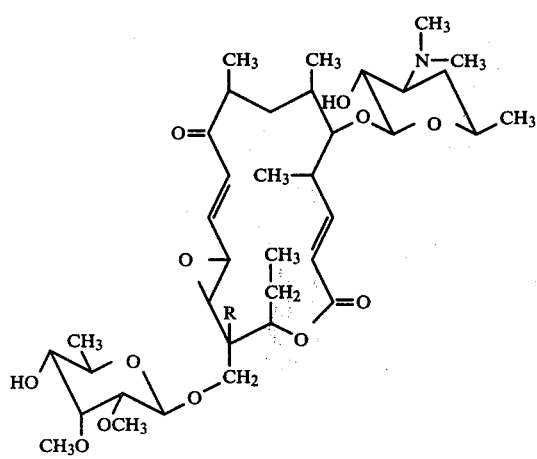

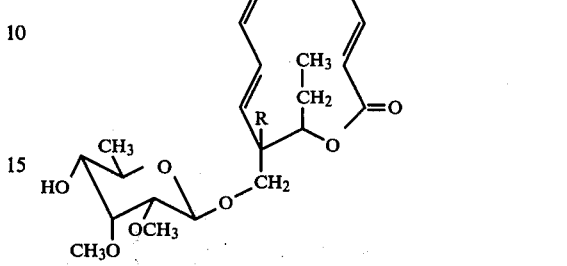

wherein in formula 1, R is hydrogen in Antibiotic AR-5 component 1 and is hydroxyl in Antibiotic AR-5 component 2 and wherein in formula 2, R is hydrogen in 12,13-desepoxy AR-5 component 1 and is hydroxyl in 12,13-desepoxy AR-5 component 2 from the medium.

2. The process of claim 1 wherein the microorganism is *Micromonospora polytrota* NRRL 12066, said microorganism also being known as *Micromonospora polytrota* ATCC 31584.

* * * * *